US005723454A

United States Patent [19]
Ban et al.

[11] Patent Number: 5,723,454
[45] Date of Patent: Mar. 3, 1998

[54] METHOD FOR OBTAINING ESTROGENS FROM PREGNANT MARE URINE BY SOLID PHASE EXTRACTION ON A SEMI-POLAR ADSORBER RESIN

[75] Inventors: Ivan Ban, Hanover; Henning Heinemann, Lehzte-Aligee; Gerhard Mechtold, Hanover; Heinz-Helmer Rasche, Burgdorf, all of Germany

[73] Assignee: Sovlay Deutschland GmbH, Hanover, Germany

[21] Appl. No.: 753,508

[22] Filed: Nov. 26, 1996

Related U.S. Application Data

[63] Continuation of Ser. No. 372,168, Jan. 12, 1995, abandoned.

[30] Foreign Application Priority Data

Feb. 8, 1994 [DE] Germany ............... 44 03 886.0
Oct. 26, 1994 [DE] Germany ............... 44 38 272.3

[51] Int. Cl.⁶ ............................................. A61K 31/56
[52] U.S. Cl. ...................... 514/169; 514/170; 514/171; 514/181; 514/182
[58] Field of Search ........................... 514/170, 169, 514/171, 181, 182

[56] References Cited

U.S. PATENT DOCUMENTS 3,769,401  10/1973  Thompson et al. .

FOREIGN PATENT DOCUMENTS 2111261  6/1972  France .

OTHER PUBLICATIONS

Zief, et al., "Preparation of Steroid Samples by Solid–Phase Extraction", *American Laboratory*, vol. 14, No. 5, May, 1982, pp. 120–130.

Tippins, "Selective Sample Preparation of Endogenous Biological Compounds Using Solid–Phase Extraction", *American Laboratory*, vol. 19, No. 2, Feb. 1987, pp. 107–114.

Heikkinen, et al., "Reversed–Phase $C_{18}$ Cartridge for Extraction of Estrogens from Urine and Plasma", *Clinical Chemistry*, vol. 27, No. 7, 1981, pp. 1186–1189.

*Primary Examiner*—John M. Cooney, Jr.
*Attorney, Agent, or Firm*—Evenson, McKeown, Edwards & Lenahan P.L.L.C.

[57] ABSTRACT

A method for obtaining an extract containing the natural mixture of conjugated estrogens from mare urine by solid-phase extraction of the mixture of conjugated estrogens from the urine of pregnant mares on non-ionic semi-polar polymeric adsorber resins.

14 Claims, No Drawings ods
METHOD FOR OBTAINING ESTROGENS FROM PREGNANT MARE URINE BY SOLID PHASE EXTRACTION ON A SEMI-POLAR ADSORBER RESIN This application is a continuation of application Ser. No. 08/372,168, filed Jan. 12, 1995 which is now abandoned.

BACKGROUND OF THE INVENTION

The present invention relates to obtaining a natural mixture of conjugated estrogens from the urine of pregnant mares.

Estrogens are used in medicine for hormone replacement therapy. In particular, estrogen mixtures are used for the treatment and prophylaxis of the disorders of the climacteric period which occur in women after natural or artificial menopause. In this case, natural mixtures of conjugated estrogens such as are found in the urine of pregnant mares have proved particularly effective and well tolerated.

The dissolved solids content in the urine of pregnant mares (=pregnant mare urine or "PMU") may naturally vary within wide ranges, and may generally lie in a range of 40–90 g dry matter per liter. In addition to urea and other usual urine contents, phenolic constituents are contained in the solids content of the PMU in quantities of about 2–5% by weight relative to dry matter. These phenolic constituents include cresols and dihydro-3,4-bis[(3-hydroxyphenyl)methyl]-2(3H)-furanone, known as HPMF. These may be present in free or conjugated form. The PMU contains a natural mixture of estrogens which is largely present in conjugated form, e.g. as sulfuric acid semi-ester sodium salt (referred to hereinafter as "sulfate salt"). The content of conjugated estrogens (calculated as estrogen sulfate salt) may be between 0.3 and 1% by weight relative to dry matter.

Usually extracts containing conjugated estrogens are obtained from the PMU by extraction with a polar organic solvent which is immiscible, or only slightly miscible, with water, such as ethyl acetate, n-butanol or cyclohexanol. In such liquid-liquid extractions, however, a number of problems occur, such as severe foaming, sedimentation, emulsification and poor phase separation. Generally several extraction steps are required, which results in losses and only partial recovery of the estrogen content.

In 1968 it was proposed by H. L. Bradlow (see Steroids 11 (1968), 265–272) to use Amberlite XAD-2®, a neutral, non-polar hydrophobic polystyrene resin, manufactured by Rohm and Haas, for the extraction of conjugated estrogens from urine. The adsorption capacity given is low. According to Bradlow, an optionally diluted urine is passed through a column containing the resin at a low rate of flow. The estrogens are eluted with methanol or ethanol. However, no details are given of the other substances contained in the estrogen-containing eluate.

Despite all the past activity in this field, there has remained a need in the art for a more effective way to recover estrogens from pregnant mare urine.

SUMMARY OF THE INVENTION

It is the object of the present invention to provide an industrial method for obtaining the natural mixture of conjugated estrogens from PMU, while avoiding the disadvantages known from the conventionally used liquid-liquid extractions, which method provides a product which is depleted in phenolic urine contents and is largely cresol-free and HPMF-free.

This and other objects of the invention are achieved by providing a method for obtaining a natural mixture, depleted in phenolic urine contents, of conjugated estrogens from the urine of pregnant mares, comprising the steps of a) contacting a mare urine material selected from the group consisting of urine freed of mucilaginous substances and solids, a concentrate formed by reducing the volume of urine freed of mucilaginous substances and solids, and a urine retentate obtained by membrane filtration of urine freed of mucilaginous substances and solids, with a sufficient quantity of a semi-polar polymeric adsorber resin to adsorb conjugated estrogens contained in the urine material, whereby a semi-polar polymeric adsorber resin charged with a mixture of adsorbed conjugated estrogens is obtained, and thereafter separating the charged adsorber resin from the rest of the urine material; b) washing the charged adsorber resin with an aqueous washing liquid having a pH of at least 12.0; and c) contacting the washed adsorber resin with a sufficient quantity of an elution liquid consisting essentially of at least one water-miscible organic solvent selected from the group consisting of water-miscible ethers, lower alkanols, and lower aliphatic ketones or of a mixture of water and at least one water-miscible organic solvent selected from the group consisting of water-miscible ethers, lower alkanols and lower aliphatic ketones, to desorb the mixture of adsorbed conjugated estrogens, and recovering an eluate containing the mixture of conjugated estrogens.

DETAILED DESCRIPTION OF PREFERRED EMBODIMENTS

A method has now been discovered with which a mixture which is largely cresol-free and HPMF-free and which is depleted in phenolic urine contents, but contains the natural estrogen content of the PMU practically in its entirety can be obtained in a solid-phase extraction on a non-ionic, semi-polar polymeric adsorber resin, which mixture can be used as a starting material for the production of pharmaceuticals containing the natural mixture of conjugated estrogens from the PMU as active ingredient.

The method according to the invention for obtaining a natural mixture, depleted in phenolic urine contents, of conjugated estrogens from PMU is characterized in that a) a liquid urine material, which represents urine freed of mucilaginous substances and solids, a reduced concentrate of such urine or a reduced urine retentate obtained by membrane filtration of such urine, is contacted with a quantity of a semi-polar polymeric adsorber resin sufficient for adsorption of the mixture of conjugated estrogens contained in the urine, and a semi-polar polymeric adsorber resin laden with the mixture of conjugated estrogens is separated from the rest of the urine, b) the semi-polar polymeric adsorber resin laden with the mixture of conjugated estrogens is washed with a washing water set to a pH range of at least 12.0, in particular of 12.5 to 14, and c) the washed adsorber resin is contacted with a quantity of an elution liquid sufficient for desorption of the mixture of conjugated estrogens adsorbed thereon, which liquid represents a water-miscible organic solvent selected from the group consisting of water-miscible ethers, lower alkanols and lower aliphatic ketones or a mixture of the water-miscible organic solvent and water which has optionally been rendered alkaline, and an eluate containing the natural mixture of conjugated estrogens is separated from the adsorber resin and optionally further concentrated by reducing it in volume.

The PMU as such, a concentrate obtained therefrom by reducing its volume or a retentate obtained therefrom by membrane filtration can be used as the starting urine material for the method according to the invention. The collected urine is first freed of mucilaginous substances and solids in a known manner. Advantageously, solids and mucilaginous substances are allowed to settle and are then separated by known separation methods, for instance decanting, separation and/or filtration. Thus the PMU can for instance be passed through a known separating apparatus, e.g. a separator, a filtration unit or a sedimenter. A sand bed, for example, may serve as a separating apparatus, or commercially-available separators, e.g. nozzle separators or chamber separators, may be used. If desired, a microfiltration apparatus or an ultrafiltration apparatus may also be used, and if they are used it is possible to obtain a substantially bacteria-free and virus-free filtered PMU at the same time.

If desired, preservatives, germicides, bactericides and/or anthelmintics can be added to the urine.

If a concentrated PMU retentate is to be used instead of the PMU, this may be obtained from the PMU by known membrane filtration. The solids content of the retentate and the composition thereof may vary according to the PMU used and the membrane used for membrane filtration, for instance the pore diameter thereof, and the conditions of the filtration. For instance, when using a nanofiltration membrane, a practically loss-free concentration of the estrogen content in the PMU retentate can be achieved with simultaneous removal of up to 50% by weight of the lower-molecular weight PMU contents. PMU retentates which have been concentrated up to a ratio of approximately 1:10, for instance a ratio of about 1:7, and the volume of which can thus be reduced to approximately 1/10, for instance about 1/7, of the original PMU volume, can be used for the method according to the invention.

The semi-polar polymeric adsorber resins which can be used in method step a) are porous organic non-ionic polymers which, in contrast to non-polar hydrophobic polymeric adsorber resins, have an intermediate polarity (=e.g. with a dipole moment of the active surface of the resin in the range of 1.0 to 3.0, in particular 1.5 to 2.0, Debye) and a somewhat more hydrophilic structure, for example polycarboxylic acid ester resins. Advantageously, macroporous semi-polar resins having a preferably macroreticular structure and average pore diameters in the range of 50 to 150, preferably 70 to 100, Angstrom, and a specific surface area in the range of 300 to 900, preferably 400 to 500, $m^2/g$ are used. Macroporous cross-linked aliphatic polycarboxylic acid ester resins, in particular cross-linked polyacrylic ester resins such as Amberlite XAD-7™, manufactured by Rohm and Haas, have proved particularly suitable.

According to the invention, the adsorption of the conjugated estrogens on the semi-polar adsorber resin can be effected by contacting the PMU or the retentate thereof with the adsorber resin, in that the urine is introduced into a reactor containing the adsorber resin and is kept in contact with the adsorber resin therein for a sufficient time for adsorption of the estrogen content. Once adsorption of the conjugated estrogens on the semi-polar adsorber resin has taken place, the adsorber resin laden with the mixture of conjugated estrogens can be separated from the rest of the urine in known manner. Advantageously, the urine can be passed through a column containing the adsorber resin at such a flow rate that the contact time is sufficient for adsorption of the estrogen content. Suitable flow rates are for instance those which correspond to a throughput of 3 to 10, preferably 5 to 7, parts by volume of PMU per one part by volume of adsorber resin per hour. The adsorption is preferably effected at room temperature. Advantageously, the rate of urine flow through the reactor can be controlled by operating at a slight overpressure or underpressure (i.e. relative to ambient pressure). The quantity of semi-polar adsorber resin to be used may vary depending on the type of adsorber resin used and the quantity of solids contained in the urine. When using PMU, for instance one part by volume adsorber resin, e.g. cross-linked aliphatic polycarboxylic acid ester adsorber resin, can be loaded or charged with up to 80 parts by volume pretreated PMU, without perceptible quantities of estrogen being detectable in the urine effluent. When using a PMU concentrate or PMU retentate, the loading capacity of the adsorber resin is of course reduced to the extent which the urine material has been concentrated. For instance, 1 part by volume cross-linked aliphatic polycarboxylic acid ester adsorber resin may be laden with a quantity of concentrated urine material corresponding to 20 to 80, preferably 30 to 50, parts by volume unconcentrated PMU.

The semi-polar adsorber resin laden with the mixture of conjugated estrogens is washed in method step b) with a washing water adjusted to a pH range of at least 12.0, in particular of 12.5 to 14, preferably about 12.5 to 13.5. Aqueous solutions of inert basic substances which are soluble in the urine and which are strong enough to reach a pH value of at least 12.5 can be used as washing liquid. Suitable water-soluble basic substances which are inert to the semi-polar polymeric adsorber resin are preferably water-soluble inorganic bases such as alkali metal or alkaline-earth metal hydroxides, in particular sodium hydroxide. Advantageously, the washing water only contains about that quantity of basic substances which is required to achieve the desired pH value, preferably approximately pH 13. The quantity of washing water is selected such that it is sufficient to substantially remove phenolic urine contents, without significant quantities of conjugated estrogens being washed out with them. For instance, the use of 2 to 10, in particular 4 to 6, bed volumes washing liquid per bed volume adsorber resin has proved advantageous. In this case, the washing water is advantageously passed through a reactor containing the adsorber resin at a throughput rate of 3 to 10, preferably 5 to 7, parts by volume of washing water per one part by volume of adsorber resin per hour.

In method step c), the washed adsorber resin laden with the mixture of adsorbed conjugated estrogens is then treated with a quantity of an elution liquid sufficient for elution of the mixture of conjugated estrogens, and an eluate containing the natural mixture of conjugated estrogens of the PMU is obtained. The elution liquid used according to the invention preferably consists essentially of a water-miscible organic solvent selected from the group consisting of water-miscible ethers, lower alkanols and lower aliphatic ketones or a mixture of such a water-miscible organic solvent and water which has optionally been rendered alkaline. Suitable ether constituents of the elution liquid include water-miscible cyclic ethers such as tetrahydrofuran or dioxane, but also water-miscible open-chain ethers such as ethylene glycol dimethyl ether (=monoglyme), diethylene glycol dimethyl ether (=diglyme) or ethyloxyethyloxy ethanol (=Carbitol). Suitable lower alkanols include water-miscible alkyl alcohols with 1 to 4, preferably 1 to 3, carbon atoms, in particular ethanol or isopropanol. Suitable lower aliphatic ketones include water-miscible ketones with 3 to 5 carbon atoms, in particular acetone. Elution liquids in which the organic solvent is ethanol have proved particularly advantageous. Advantageously, mixtures of one of the aforementioned water-miscible organic solvents and water which has optionally been rendered alkaline are used as elution liquids. The pH value of such water-containing eluents is in the neutral to alkaline range up to pH 13 and may advantageously be approximately 10 to 12. A solvent which is stable in the pH range used is selected as the solvent component in the water-containing elution liquid. In water-containing alkaline elution liquids having pH values of approximately 10 to 12, lower alkanols, preferably ethanol, are particularly suitable as solvent components. The desired pH value of the water-containing eluent is achieved by adding a corresponding quantity of a water-soluble inert basic substance, preferably an inorganic base, for instance an alkali metal or alkaline earth metal hydroxide, in particular sodium hydroxide. In water-containing elution liquids there may be a volume ratio of water-miscible organic solvent to water in the range of 40:60 to 20:80, preferably approximately 30:70. The quantity of eluent used may be approximately 3 to 10, in particular approximately 4 to 6, bed volumes of elution liquid per bed volume of adsorber resin. Advantageously, the elution liquid is passed through a reactor containing the adsorber resin laden with the estrogen mixture at such a flow rate that the contact time is sufficient for complete elution of the mixture of conjugated estrogens. When using a mixture of ethanol with water in a volume ratio of 30:70, for instance flow rates of 3 to 10, preferably 5 to 7, parts by volume elution liquid per 1 part per volume adsorber resin per hour are suitable. Advantageously, the elution is performed at a temperature in the range from room temperature to approximately 60° C., preferably at approximately 40° to 50° C. If desired, the flow rate is regulated by operating at slightly elevated pressure, e.g. at an overpressure of up to 0.2 bar (relative to ambient pressure), and the eluate is collected in several fractions. The conjugated estrogen content and the content of phenolic urine ingredients such as cresols and HPMF in the individual eluate fractions may be determined in known manner by high-performance liquid chromatography ("HPLC").

Upon elution, a slightly-colored to colorless, practically estrogen-free preliminary fraction is initially obtained, the quantity of which generally corresponds to approximately one bed volume. The bulk of the conjugated estrogens, for instance between 80 and 99% of the conjugated estrogens present in the starting PMU, is in the subsequent dark-yellow-brown colored main eluate fractions, the quantity of which is generally 2 to 4 bed volumes. Generally only traces of conjugated estrogens are contained in the subsequent afterrun fractions. If succeeding fractions are obtained which still have a conjugated estrogen content of above 10% by weight relative to dry matter and a content of cresols and HPMF of less than 0.6% by weight relative to dry matter, these may be combined with the estrogen-rich main eluate for further processing.

The main eluate separated from the adsorber resin in the manner previously described contains the natural mixture of conjugated estrogens occurring in the PMU in addition to only a small proportion of the phenolic urine ingredients originally present in the PMU. This eluate may be used as a starting material for producing medicaments containing the natural mixture of conjugated estrogens. If desired, the volume of the eluate may be further reduced in known manner in order to obtain a concentrate substantially free of organic solvent which is suitable for further galenic processing. If desired, an eluent-free solids mixture can also be produced by spray-drying. If the natural mixture of conjugated estrogens is to be used for producing solid medicaments, it may be advantageous to admix a solid carrier material with the eluate containing the conjugated estrogens before concentration or spray-drying, in order to obtain in this manner a solids mixture containing the conjugated estrogens and the carrier. Both the eluate containing the estrogen mixture and a concentrate produced therefrom or spray-dried solids product may be processed in a known manner into solid or liquid galenic preparations such as tablets, dragees, capsules or emulsions. These galenic preparations can be produced by known methods using conventional solid or liquid carriers such as starch, cellulose, lactose or talcum, or liquid paraffins and/or using conventional pharmaceutical adjuvants, such as tablet disintegrating agents, solubilizers or preservatives. For instance, the product containing the conjugated estrogens may be mixed in a known manner with the pharmaceutical carrier material and adjuvants and the resulting mixture converted into a suitable dosage form.

The following examples are intended to illustrate the invention in further detail without restricting its scope.

EXAMPLES 1–3

General operating procedure for obtaining an extract from PMU which is largely depleted in phenolic urine contents and contains the natural mixture of the conjugated estrogens contained in the PMU.

A) Adsorption of the estrogen content of the PMU on a semi-polar polyacrylic ester adsorber resin A column having a height of 30 cm and a diameter of 2.4 cm was filled with 65 ml of a semi-polar polyacrylic ester adsorber resin (=Amberlite XAD-7™, manufactured by Rohm and Haas, grain size 0.3 to 1.2 mm, dipole moment 1.8 Debye, average pore diameter 80 Angstrom, specific surface area approximately 450 $m^2$/g dry) swollen in water. 2 liters of a PMU (for dry matter content (=DM) and also contents of estrone sulfate salt, cresol and HPMF determined by means of HPLC see following table of examples) filtered through a microfiltration unit or purified by passing through a separator were passed through the column at room temperature at a flow rate of 6 ml/min. (=approximately 5.5 bed volumes per hour). The estrogen content of the PMU was fully adsorbed on the semi-polar adsorber resin column. The estrone sulfate salt content of the urine effluent was determined by HPLC, and the effluent proved to be practically estrogen-free. The bottom product was discarded.

B) Washing of the laden adsorber resin column

The estrogen-charged adsorber resin column was washed with 300 ml of an aqueous sodium hydroxide solution having the pH value given in the table of examples. To this end, the alkaline washing water was passed through the column at a flow rate of 6 ml/min. (=approximately 5.5. bed volumes per hour). The contents of estrone sulfate salt, cresol and HPMF in the washing liquid effluent were analyzed by HPLC. The analysis showed that less than 5% of the total estrogens charged onto the column was washed out during the washing phase.

C) Desorption of the conjugated estrogens from the washed adsorber resin column 315 ml of the elution liquid (water/solvent mixture rendered alkaline by the addition of sodium hydroxide, for composition and pH see following table of examples) were passed through the column, which had been preheated to the elution temperature given in the table of examples, at a flow rate of approximately 6 ml/min. The eluate running off was collected in 6 fractions. The first fraction was about 65 ml (=approximately 1 bed volume), and the remaining fractions were each about 50 ml. The contents of estrone sulfate salt, cresol and HPMF in the individual fractions were analyzed by HPLC. The first fraction was collected for as long as the eluate appeared colorless to slightly yellowish in color. This fraction contained only traces of estrogen sulfate salt.

Once the first bed volume of eluate had run off, the color of the eluate changed to an intensive dark-brown color. Then approximately 80 to 98% of the total quantity of conjugated estrogens adsorbed on the column were contained in the subsequent fractions 2 to 4. The remaining fractions contained only a small quantity of estrogen sulfate salt. This could also clearly be seen in the decrease in color intensity. Optionally, the remaining fractions can be returned to method step a) after the solvent content has been distilled off.

The dry matter content in % by weight and the respective contents of estrone sulfate salt, cresol and HPMF determined by HPLC are given in the following table of examples for the fractions containing the majority of the conjugated estrogens. These fractions represent extracts suitable for further galenic processing.

Regeneration of the adsorber resin column

In order to regenerate the column, it was first washed with 100 ml of an ethanol/water mixture containing 50% ethanol and having a pH of 12, then with 150 ml 10% aqueous sodium citrate solution and again with 150 ml of the ethanol/water mixture, and finally with 100 ml of distilled water. The entire regeneration took place at a temperature of 45° C. The column can be charged and regenerated many times, for instance up to 40 times.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method for obtaining a natural mixture, depleted in phenolic urine contents, of conjugated estrogens from the urine of pregnant mares, said method comprising the steps of:

a) contacting a mare urine material selected from the group consisting of urine freed of mucilaginous substances and solids, a concentrate formed by reducing the volume of urine freed of mucilaginous substances and solids, and a urine retentate obtained by membrane filtration of urine freed of mucilaginous substances and solids, with a sufficient quantity of a semi-polar polymeric adsorber resin to adsorb conjugated estrogens contained in the urine material, whereby a semi-polar polymeric adsorber resin charged with a mixture of adsorbed conjugated estrogens is obtained, and thereafter separating the charged adsorber resin from the rest of the urine material;

b) washing the charged adsorber resin with an aqueous washing liquid having a pH of at least 12.0; and c) contacting the washed adsorber resin with a sufficient quantity of an elution liquid consisting essentially of at least one water-miscible organic solvent selected from the group consisting of water-miscible ethers, lower alkanols, and lower aliphatic ketones or of a mixture of water and at least one water-miscible organic solvent selected from the group consisting of water-miscible ethers, lower alkanols and lower aliphatic ketones, to desorb the mixture of adsorbed conjugated estrogens, and recovering an eluate containing the mixture of conjugated estrogens.

2. A method according to claim 1, wherein said elution liquid is a mixture of water which has been adjusted to have an alkaline pH and at least one water-miscible organic solvent selected from the group consisting of water-miscible ethers, lower alkanols, and lower aliphatic ketones.

3. A method according to claim 1, further comprising reducing the volume of the recovered eluate to obtain a concentrated eluate containing the mixture of conjugated estrogens.

| Example No. | | 1 | | 2 | | 3 | |
|---|---|---|---|---|---|---|---|
| Starting PMU | | | | | | | |
| Weight percent dry matter (DM) | | 7.3 | | 6.5 | | 7.1 | |
| Estrogen sulfate salt content | mg/l (wt-% DM) | 110 | (0.15) | 125 | (0.19) | 124 | (0.17) |
| Cresol content | mg/l (wt-% DM) | 232 | (0.32) | 263 | (0.40) | 269 | (0.38) |
| HPMF content | mg/l (wt-% DM) | 74 | (0.10) | 86 | (0.13) | 88 | (0.12) |
| Washing Liquid = aqueous NaOH solution | | pH 12.5 | | pH 13.0 | | pH 13.5 | |
| Elution Liquid | | Ethanol/Water 30:70 pH 12 | | Ethanol/Water 30:70 pH 12 | | Ethanol/Water 30:70 pH 12 | |
| Elution Temperature | | 45° C. | | 45° C. | | 45° C. | |
| Elution Fraction 2 | | | | | | | |
| Weight percent dry matter (DM) | | 1.0 | | 1,5 | | 3.9 | |
| Estrogen sulfate salt content | mg/l (wt-% DM) | 2241 | (22.41) | 2217 | (14.78) | 1461 | (3.75) |
| Cresol content | mg/l (wt-% DM) | 112 | (1.12) | 82 | (0.55) | 161 | (0.41) |
| HPMF content | mg/l (wt-% DM) | 0 | (0.00) | 0 | (0.00) | 0 | (0.00) |
| Elution Fraction 3 | | | | | | | |
| Weight percent dry matter (DM) | | 1.6 | | 0.7 | | 1.2 | |
| Estrogen sulfate salt content | mg/l (wt-% DM) | 1625 | (10.16) | 1731 | (24.73) | 2201 | (18.34) |
| Cresol content | mg/l (wt-% DM) | 62 | (0.39) | 0 | (0.00) | 59 | (0.49) |
| HPMF content | mg/l (wt-% DM) | 2 | (0.01) | 0 | (0.00) | 0 | (0.00) |
| Elution Fraction 4 | | | | | | | |
| Weight percent dry matter (DM) | | 0.1 | | 0.1 | | 0.4 | |
| Estrogen sulfate salt content | mg/l (wt-% DM) | 240 | (24.00) | 285 | (28.50) | 652 | (16.30) |
| Cresol content | mg/l (wt-% DM) | 16 | (1.60) | 9 | (0.90) | 9 | (0.22) |
| HPMF content | mg/l (wt-% DM) | 3 | (0.30) | 0 | (0.00) | 2 | (0.05) |

4. A method according to claim 1, wherein said semi-polar adsorber resin is a macroporous polycarboxylic acid ester resin.

5. A method according to claim 4, wherein said polycarboxylic acid ester resin is a cross-linked aliphatic polycarboxylic acid ester resin.

6. A method according to claim 5, wherein said cross-linked polycarboxylic acid ester resin has a macroreticular structure.

7. A method according to claim 1, wherein in step a) one part by volume of semi-polar adsorber resin is contacted with an amount of urine material corresponding to from 20 to 80 parts by volume of pregnant mare urine.

8. A method according to claim 7, wherein one part by volume of semi-polar adsorber resin is contacted with an amount of urine material corresponding to from 30 to 50 parts by volume of pregnant mare urine.

9. A method according to claim 1, wherein step a) is carried out by passing the urine material through a vessel containing the semi-polar polymeric adsorber resin at a flow rate corresponding to from 3 to 10 parts by volume of urine per one part by volume of adsorber resin per hour.

10. A method according to claim 9, wherein the urine material is passed through the vessel at a flow rate corresponding to from 5 to 7 parts by volume of urine per one part by volume of adsorber resin per hour.

11. A method according to claim 1, wherein in step b) the aqueous washing liquid is an aqueous sodium hydroxide solution having a pH of about 12.5 to 13.5.

12. A method according to claim 1, wherein in step c) the elution liquid is a mixture of water and a water-miscible organic solvent comprising a volume ratio of organic solvent to water in the range from 20:80 to 40:60.

13. A method according to claim 12, wherein the elution liquid comprises a 30:70 volume ratio of organic solvent to water.

14. A method according to claim 1, wherein in step c) the elution liquid comprises ethanol.

* * * * *

UNITED STATES PATENT AND TRADEMARK OFFICE
CERTIFICATE OF CORRECTION

PATENT NO. : 5,723,454
DATED : March 3, 1998
INVENTOR(S) : Ivan BAN et al.

It is certified that error appears in the above-identified patent and that said Letters Patent is hereby corrected as shown below:

Title page,
    item [73]    Change the name of the Assignee from "Sovlay Deutschland GmbH" to --Solvay Deutschland GmbH--.

Title page,
    item [75]    Change the residence of the second inventor Henning Heinemann from "Lehzte-Aligee" to --Lehrte-Aligse--.

Signed and Sealed this

Twelfth Day of January, 1999

Attest:

Attesting Officer    *Acting Commissioner of Patents and Trademarks*